United States Patent [19]

Ray et al.

[11] Patent Number: 5,679,510
[45] Date of Patent: Oct. 21, 1997

[54] QUANTITATIVE DETECTION OF SPECIFIC NUCLEIC ACID SEQUENCES USING LAMBDOID BACTERIOPHAGES LINKED BY OLIGONUCLEOTIDES TO SOLID SUPPORT

[75] Inventors: Bryan L. Ray, Burlington; Edmund C. C. Lin, Boston, both of Mass.

[73] Assignee: Hybridon, Inc., Cambridge, Mass.

[21] Appl. No.: 368,870

[22] Filed: Jan. 5, 1995

Related U.S. Application Data

[63] Continuation-in-part of Ser. No. 53,866, Apr. 27, 1993, abandoned.
[51] Int. Cl.$^6$ .............. C12Q 1/70; C12Q 1/68; C12Q 1/02; C12P 19/34
[52] U.S. Cl. .............. 435/5; 435/6; 435/29; 435/37; 435/91.2; 435/181
[58] Field of Search ................ 435/5, 6, 91.2, 435/29, 39, 181

[56] References Cited

U.S. PATENT DOCUMENTS

| | | | |
|---|---|---|---|
| 3,717,705 | 2/1973 | Haimovich et al. | 424/12 |
| 4,775,619 | 10/1988 | Urdea | 435/6 |
| 4,917,998 | 4/1990 | Burger et al. | 435/5 |
| 5,118,605 | 6/1992 | Urdea | 435/6 |
| 5,168,037 | 12/1992 | Entis et al. | 435/5 |

FOREIGN PATENT DOCUMENTS

| | | |
|---|---|---|
| 0 439 222 A2 | 7/1991 | European Pat. Off. |
| 0 455 517 A1 | 11/1991 | European Pat. Off. |
| 0 455 905 A2 | 11/1991 | European Pat. Off. |
| WO89/09284 | 10/1989 | WIPO |
| WO91/17264 | 11/1991 | WIPO |

OTHER PUBLICATIONS

Mifflin et al, (1989), "Use and applications of Nucleic Acid Probes in the Clinical Laboratory", Clin. Chem. 35(9):1819–1825.

Hsu et al, (1977), "A bacteriophage system for screening and study of biologically active polycyclic aromatic hydrocarbons and related compounds", Proc. Natl. Acad Sci 74(4):1378–1382.

Sternberg, Steve. Biotech Challenged To Close HIV Window In Blood Donor Screening. *BioWorld Today;* vol. 5, No. 189, Thursday, Sep. 29, 1994, p. 1.

Hamilton, Joan O'C.. A Virus Sleuth Called DNA: *Business Week,* Apr. 4, 1994, p. 93.

Piercey, Lisa. FDA Proposes Expert Advisory Group On Surrogate Markers. *BioWorld Today;* vol. 5, No. 210, Friday, Oct. 28, 1994, p. 1.

Piercey, Lisa. Viral Load Monitoring Tool May Help AIDS Researchers. *BioWorld Today;* vol. 5, No. 208, Wednesday, Oct. 26, 1994, p. 2.

(List continued on next page.)

Primary Examiner—George G. Elliott
Assistant Examiner—Jeffrey Fredman
Attorney, Agent, or Firm—Ann-Louise Kerner, Ph.D.; Hale and Dorr LLP

[57] ABSTRACT

The present invention provided compositions, methods and kits for detection and quantitation of pathogenic organisms. The composition of the invention is an oligonucleotide probe comprising a bacteriophage covalently linked to one site on an oligonucleotide probe complementary to a conserved region of a pathogenic organism. At a second site, the oligonucleotide probe is linked to a matrix. The oligonucleotide probe contains a region complementary to one strand of a restriciton endonuclease recognition site or an oligoribonucleotide moiety. The number of pathogenic organisms present in a biological fluid sample may be quantitated in accordance with the method of the invention by combining the composition of the invention with the sample, allowing hybridization to occur. Hybridization generates a DNA-RNA hybrid, and by adding the appropriate nucleolytic enzyme capable of cleaving DNA-RNA hybrids; bacteriophage will be released for measurement. The kit of the invention provides components which allow the method of the invention to be performed.

5 Claims, 2 Drawing Sheets

OTHER PUBLICATIONS

Landegren, Ulf. Molecular mechanics of nucleic acid sequence amplification. *Trends in Genetics;* vol. 9 No. 6, Jun. 1993, pp. 199–203.

Krajden, Mel. The role of moelcular biology in the characterization and clinical detection of HCV. *Clinical Chemistry News;* Jun. 1994, vol. 20, No. 6, p. 5.

Urdea, Mickey S. et al. *Luminescence Immunoassay and Molecular Applications:* A novel method for the rapid detection of Hepatitis B virus in human serum samples without blotting or radioactivity. Knox Van Dyke, Ed. CRC Press: Boca Raton, FL: 1990, pp. 275–292.

Craig, Charles. ID Biomedical Signs Deals With Italian Firm for Hepatitis Test. *BioWorld Today;* Wednesday, Aug. 24, 1994, p. 2.

Business Wire: Chiron's Quantiplex HCV RNA bDNA probe assay licensed in Japan for sale by Daiichi Pure Chemical. Mar. 31, 1994.

Business Wire: Chiron HCV patent application is published for opposition in Japan, Dec. 14, 1993.

Danheiser, Susan L. Advances in DNA Probe–Based Assays Lead to Second–Generation Products. *Genetic Engineering News,* Jun. 15, 1994, pp. 6–7.

QUANTITATIVE DETECTION OF SPECIFIC NUCLEIC ACID SEQUENCES USING LAMBDOID BACTERIOPHAGES LINKED BY OLIGONUCLEOTIDES TO SOLID SUPPORT

This application is a continuation-in-part of commonly assigned application Ser. No. 08/053,866 entitled "Method of Detecting Compounds Utilizing Chemically Modified Lambdoid Bacteriophage", filed Apr. 27, 1993, now abandoned.

The present invention relates to the field of assay for specific nucleic acid sequences such as those which are found in pathogenic organisms. More particularly, the present invention is directed to quantitative detection of nucleic acid sequences characteristic of pathogens, as an aid to diagnosing and treating diseases caused or exacerbated by those pathogens.

BACKGROUND OF THE INVENTION

A very large number of diseases are caused worldwide by pathogenic organisms such as viruses, bacteria, protozoans, multicellular parasites, and the like. Although diagnosis, prevention, and treatment of many such diseases have advanced as a direct result of improved assay techniques for detection of the causative pathogens, only one viral disease, smallpox, has been eradicated. Pathogenic organisms continue to cause significant health problems for humans and for animals. For example, drug resistant *Mycobacterium tuberculosis* has become an increasing health problem requiring rapid and accurate detection. *Escherichia coli* 0157:H7, a contaminant found in meat, has recently caused a significant outbreak of food poisoning. *Borrelia burgdorferi* is difficult to detect accurately in biological samples, causing corresponding difficulty in early and accurate diagnosis of Lyme Disease. Protozoan organisms such as the Plasmodium species which cause malaria, the various Leishmania species, and the Toxoplasma species are all also difficult to detect accurately at early stages of infection. Many other pathogenic diseases remain to plague humans and other animals and to exact a huge toll in terms of life expectancy, quality of life, and economic loss.

Thus far a number of diagnostic tests are commercially available which can detect the presence or absence of pathogenic organisms. For example, assays are available for detection of hepatitis B virus, hepatitis C virus, human immunodeficiency virus, Toxoplasma, Entamoeba, Chlamydia, Borrelia, and the like. However, commercially available assays are limited in their ability to quantitate the number of pathogenic organisms present in a particular biological fluid.

Quantitative assays have several benefits over non-quantitative assays. First, quantitative assays are essential in monitoring the effectiveness of treating diseases. To evaluate whether or not a treatment is effective, a method for accurately measuring the number of pathogenic organisms present in the infected animal may be essential. Second, quantitative assays are necessary for evaluating the efficacy of new drugs for treatment. Third, quantitative assays can be used to verify the presence of pathogenic organisms in biological fluid samples that have qualitatively tested positive by less sensitive methods.

The first assays developed for pathogenic organisms were immunoassays designed to detect the presence of antibodies produced by an infected animal in response to viruses such as hepatitis B virus (HBV) and hepatitis C virus (HCV). The immunoassays used viral antigens, which are portions of the virus, in order to detect antibodies specific for those antigens present in body fluids, such as serum, plasma, saliva, cerebrospinal fluid, and the like. The so-called first-generation immunoassays provided only a single viral antigen and thus were not very sensitive. Second- and third-generation immunoassays were later developed which used combinations of viral antigens and therefore had greater sensitivity. However, infection is not detectable by these immunoassays until the animal produces antibodies against the pathogenic organism, a process which can take a significant amount of time, depending on the organism. For example, HCV antibodies are first detected in serum from 10 to 52 weeks after infection with a mean lag of 15 weeks. Second-generation tests have shortened this period, but there continues to be a time period during which the presence of pathogens cannot be detected using immunologic methods.

Another, less sensitive kind of immunoassay contains antibodies that detect the presence of pathogen antigens in the biological fluid. Using these assays, the titer of the pathogenic organism in the biological fluid must be high enough to produce a signal, which may also result in a significant lag between the time of infection and the time that infection can be detected. For infections characterized by sequestering of the pathogen within an organ, such that the pathogen is not shed into a biological fluid, this kind of assay is completely ineffective.

Thus, each of the available immunologic methods of detecting pathogen infections has deficiencies. The current immunoassays are not quantitative, because they do not directly measure the levels of pathogen particles present. Currently available immunoassays are ineffective at early stages of infection, when the antibody or pathogen titer is low. Moreover, methods which are based on a humoral immune response are ineffective for detection of pathogens which elicit a cellular immune response.

Sequencing of pathogen genomes has allowed development of assays that detect the presence of the pathogen genome in a biological fluid. DNA sequence-based assays directly or indirectly measure the level of pathogen genome present in biological fluids. This class of diagnostics can be divided into two subclasses: assays that rely on amplification of the pathogen genome to detectable levels; and assays that use probes that bind to areas of the pathogen genome.

The most common method of amplifying the pathogen genome employs the polymerase chain reaction (PCR). PCR can be quantitative, and PCR-based assays can be very sensitive. For example, PCR-based assays are able to detect viral RNA within one to two weeks after infection. There are, however, problems with the current PCR technology. First, the limit for detection of PCR-based diagnostics for HCV, for example, is approximately 2000 RNA genomes per milliliter of serum. Second, because of the lack of standardized protocols, results may vary greatly from laboratory to laboratory. Moreover, PCR-based tests require specialized equipment and training of laboratory personnel. Furthermore, because the technology is based on amplifying the level of the original RNA or DNA, the procedure is very susceptible to contamination and inaccuracies in the amplification that are inherent to the PCR procedure. Although a PCR-based test for HCV is currently in clinical trials in the United States, to date, no PCR-based test for a pathogen has received FDA approval. Thus PCR-based tests are currently only used for research, and at best, because of the complexity of the technology, commercial PCR-based assays may only be appropriate for use in reference laboratories.

Two genomic probe-based assays for HCV have been developed. Current genomic probe-based technologies have been hampered by the lack of probes that can detect extremely small quantities of pathogen genome, such as 1 to 100 molecules. For example, one assay, based on a branched DNA probe, has gained approval in Japan. The limit of detection with this method is approximately 350,000 genomes per milliliter of serum. Furthermore, when ultrasensitive probes are utilized, the problem of high background signals, or noise, becomes an issue. Such noise is a result of nonspecific binding of the probe. Thus although the probe-based technologies do not have the problems associated with PCR, these assays lack the high sensitivity of the PCR-based tests.

Thus a need continues to exist for novel, quantitative, DNA-based diagnostics which detect pathogenic agents. Such novel DNA-based diagnostics should be as sensitive as, or more sensitive than PCR-based assays, and further should not have the problems involved with currently available genomic probe-based assays.

SUMMARY OF THE INVENTION

The present inventors have discovered a method for quantitating the extent of infection of a mammal by a pathogenic organism. The method of the invention measures the number of pathogen genomes present in a biological fluid which hybridize to an oligonucleotide probe complementary to a portion of the pathogen genome. The oligonucleotide probe is attached via a functional group present on a first nucleic acid residue or site to a matrix and via a functional group present on a second nucleic acid residue or site to a bacteriophage. In accordance with the method of the invention, after hybridization has occurred, the oligonucleotide probe-matrix-pathogen genome complex is treated with a restriction endonuclease capable of cleaving a specific sequence of DNA present in the probe. The specific double stranded sequence cleaved by the restriction endonuclease is produced by the hybridization of the oligonucleotide probe to the pathogen genome. Treatment of the complex with the restriction endonuclease releases infective bacteriophage, which may be measured by adding the bacteriophage to a bacterial host strain, allowing infection to proceed, and counting the number of bacteriophage plaques produced. In this way the number of pathogenic organisms in a biological fluid may be quantitated without DNA amplification and without the background problems associated with other genomic probe-based assays.

In one embodiment, the invention provides a composition comprising: a lambdoid bacteriophage; a single stranded oligonucleotide; and a matrix, wherein a surface polypeptide of the bacteriophage is covalently linked to one site on the oligonucleotide and the matrix is linked to another site on the oligonucleotide, and the oligonucleotide is characterized by a nucleic acid sequence complementary to a conserved and distinctive region of a genome of a pathogenic organism. In some embodiments, the nucleic acid sequence is also complementary to one strand of a restriction endonuclease recognition site.

In another embodiment, the invention comprises a method for quantitating a pathogenic organism in a biological fluid, the pathogenic organism being characterized by a genome having a restriction endonuclease recognition site near a desired conserved region of the genome, which method comprises:

a. combining the biological fluid with an oligonucleotide probe comprising a lambdoid bacteriophage having a surface polypeptide covalently linked to one site on a single stranded oligonucleotide, said oligonucleotide being linked via a second site to a matrix and being characterized by a nucleic acid sequence complementary to the conserved region of the genome of the pathogenic organism and to one strand of the restriction endonuclease recognition site;

b. incubating the biological fluid and the oligonucleotide probe at a temperature and for a time sufficient to allow nucleic acid hybridization to occur, thereby forming a hybridization mixture;

c. incubating the hybridization mixture with a restriction endonuclease at a temperature and for a time sufficient to allow cleavage of all nucleic acids containing the restriction endonuclease recognition site, thereby releasing infective lambdoid bacteriophage;

d. measuring the number of infective lambdoid bacteriophage released in step c.

In another embodiment, the invention provides a kit comprising:

a. a lambdoid bacteriophage having a surface polypeptide covalently linked to one site on a single stranded oligonucleotide, said oligonucleotide being linked via a second site to a matrix and being characterized by a nucleic acid sequence complementary to a conserved region of a genome of a pathogenic organism and to one strand of a restriction endonuclease recognition site;

b. a bacterial strain capable of becoming infected by the lambdoid bacteriophage; and c. a restriction endonuclease capable of cleaving the oligonucleotide.

In yet another embodiment, the invention provides a composition comprising a lambdoid bacteriophage; a single stranded oligoribonucleotide; and a matrix, wherein a surface polypeptide of the bacteriophage is covalently linked to one site on the oligoribonucleotide and the matrix is linked to another site on the oligoribonucleotide, and the oligoribonucleotide is characterized by a nucleic acid sequence complementary to a conserved region of a genome of a pathogenic organism.

The invention is further embodied as a method for quantitating a pathogenic organism in a biological fluid, the pathogenic organism being characterized by a double stranded genome, which method comprises:

a. combining the biological fluid with an oligoribonucleotide probe comprising a lambdoid bacteriophage having a surface polypeptide covalently linked to one site on a single stranded oligoribonucleotide, said oligoribonucleotide being linked via a second site to a matrix and being characterized by a nucleic acid sequence complementary to the conserved region of the genome of the pathogenic organism;

b. incubating the biological fluid and the oligoribonucleotide probe at a temperature and for a time sufficient to allow nucleic acid hybridization to occur, thereby forming a hybridization mixture;

c. incubating the hybridization mixture with a nucleolytic enzyme capable of clearing DNA-RNA hybrids at a temperature and for a time sufficient to allow cleavage of all deoxyribonucleic acid-ribonucleic acid hybrids, thereby releasing infective lambdoid bacteriophage;

d. measuring the number of infective lambdoid bacteriophage released in step c.

In another embodiment, the invention provides a kit comprising:

a. a lambdoid bacteriophage having a surface polypeptide covalently linked to one site on a single stranded oligoribonucleotide, said oligoribonucleotide being linked via a second site to a matrix, and being characterized by a nucleic acid sequence complementary to a conserved region of a genome of a pathogenic organism;

b. a bacterial strain capable of becoming infected by the lambdoid bacteriophage; and c. a ribonuclease capable of cleaving deoxyribonucleic acid-ribonucleic acid hybrids.

In another embodiment, the invention provides a composition comprising a bacteriophage capable of infecting *Bacillus subtilis*; a single stranded oligonucleotide; and a matrix, wherein a surface polypeptide of the bacteriophage is covalently linked to one site on the oligonucleotide and the matrix is linked to another site on the oligonucleotide, and the oligonucleotide is characterized by a nucleic acid sequence complementary to a conserved region of a genome of a pathogenic organism.

In another embodiment, the invention provides a method for quantitating a pathogenic organism in a biological fluid, the pathogenic organism being characterized by a single stranded genome having a restriction endonuclease recognition site near a conserved region of the genome, which method comprises:

a. combining the biological fluid with an oligonucleotide probe comprising a bacteriophage capable of infecting *Bacillus subtilits*, said bacteriophage having a surface polypeptide covalently linked to one site on a single stranded oligonucleotide, said oligonucleotide being linked via a second site to a matrix and being characterized by a nucleic acid sequence complementary to the conserved region of the genome of the pathogenic organism and to one strand of the restriction endonuclease recognition site;

b. incubating the biological fluid and the oligonucleotide probe at a temperature and for a time sufficient to allow nucleic acid hybridization to occur, thereby forming a hybridization mixture;

c. incubating the hybridization mixture with a restriction endonuclease at a temperature and for a time sufficient to allow cleavage of all nucleic acids containing the restriction endonuclease recognition site, thereby releasing infective bacteriophage;

d. measuring the number of infective bacteriophage released in step c.

In another embodiment, the invention provides a kit comprising:

a. a bacteriophage capable of infecting *Bacillus subtilis*, said bacteriophage having a surface polypeptide covalently linked to one site on a single stranded oligonucleotide, said oligonucleotide being linked via a second site to a matrix, and being characterized by a nucleic acid sequence complementary to a conserved region of a genome of a pathogenic organism and one strand of a restriction endonuclease recognition site;

b. a bacterial strain capable of becoming infected by the bacteriophage; and c. a restriction endonuclease capable of cleaving at the restriction endonuclease recognition site.

In another embodiment, the invention provides a method for quantitating a pathogenic organism in a biological fluid, the pathogenic organism being characterized by a double stranded genome, which method comprises:

a. combining the biological fluid with an oligoribonucleotide probe comprising a bacteriophage capable of infecting *Bacillus subtilis*, said bacteriophage having a surface polypeptide covalently linked to one site on a single stranded oligoribonucleotide, said oligoribonucleotide being linked via a second site to a matrix and being characterized by a nucleic acid sequence complementary to the conserved region of the genome of the pathogenic organism;

b. incubating the biological fluid and the oligoribonucleotide probe at a temperature and for a time sufficient to allow nucleic acid hybridization to occur, thereby forming a hybridization mixture;

c. incubating the hybridization mixture with a ribonuclease at a temperature and for a time sufficient to allow cleavage of all deoxyribonucleic acid-ribonucleic acid hybrids, thereby releasing infective bacteriophage;

d. measuring the number of infective bacteriophage released in step c.

In another embodiment, the invention provides a kit comprising:

a. a bacteriophage capable of infecting *Bacillus subtilis*, said bacteriophage having a surface polypeptide covalently linked to one site on a single stranded oligoribonucleotide, said oligoribonucleotide being linked via a second terminus to a matrix, and being characterized by a nucleic acid sequence complementary to a conserved region of a genome of a pathogenic organism;

b. a bacterial strain capable of becoming infected by the lambdoid bacteriophage; and c. a ribonuclease capable of cleaving deoxyribonucleic acid-ribonucleic acid hybrids.

In yet another embodiment, the invention provides a composition comprising a bacteriophage capable of infecting *Lactobacillus lactis*; a single stranded oligonucleotide; and a matrix, wherein a surface polypeptide of the bacteriophage is covalently linked to one site on the oligonucleotide and the matrix is linked to another site on the oligonucleotide, and the oligonucleotide is characterized by a nucleic acid sequence complementary to a conserved region of a genome of a pathogenic organism.

In another embodiment, the invention provides a method for quantitating a pathogenic organism in a biological fluid, the pathogenic organism being characterized by a single stranded genome having a restriction endonuclease recognition site near a conserved region of the genome, which method comprises:

a. combining the biological fluid with an oligonucleotide probe comprising a bacteriophage capable of infecting *Lactobacillus lactis*, said bacteriophage having a surface polypeptide covalently linked to one site on a single stranded oligonucleotide, said oligonucleotide being linked via a second site to a matrix and being characterized by a nucleic acid sequence complementary to the conserved region of the genome of the pathogenic organism and to one strand of the restriction endonuclease recognition site;

b. incubating the biological fluid and the oligonucleotide probe at a temperature and for a time sufficient to allow nucleic acid hybridization to occur, thereby forming a hybridization mixture;

c. incubating the hybridization mixture with a restriction endonuclease at a temperature and for a time sufficient to allow cleavage of all nucleic acids containing the restriction endonuclease recognition site, thereby releasing infective bacteriophage;

d. measuring the number of infective bacteriophage released in step c.

In another embodiment, the invention provides, a kit comprising:

a. a bacteriophage capable of infecting *Lactobacillus lactis*, said bacteriophage having a surface polypeptide covalently linked to one site on a single stranded oligonucleotide, said oligonucleotide being linked via a second site to a matrix, and being characterized by a nucleic acid sequence complementary to a conserved region of a genome of a pathogenic organism and one strand of a restriction endonuclease recognition site;

b. a bacterial strain capable of becoming infected by the bacteriophage; and c. a restriction endonuclease capable of cleaving at the restriction endonuclease recognition site.

In another embodiment, the invention provides a method for quantitating a pathogenic organism in a biological fluid, the pathogenic organism being characterized by a double stranded genome, which method comprises:

a. combining the biological fluid with an oligoribonucleotide probe comprising a bacteriophage capable of infecting *Lactobacillus lactis*, said bacteriophage having a surface polypeptide covalently linked to one site on a single stranded oligoribonucleotide, said oligoribonucleotide being linked via a second site to a matrix and being characterized by a nucleic acid sequence complementary to the conserved region of the genome of the pathogenic organism;

b. incubating the biological fluid and the oligoribonucleotide probe at a temperature and for a time sufficient to allow nucleic acid hybridization to occur, thereby forming a hybridization mixture;

c. incubating the hybridization mixture with a ribonuclease at a temperature and for a time sufficient to allow cleavage of all deoxyribonucleic acid-ribonucleic acid hybrids, thereby releasing infective bacteriophage;

d. measuring the number of infective bacteriophage released in step c.

In another embodiment, the invention provides a kit comprising:

a. a bacteriophage capable of infecting *Lactobacillus lactis*, said bacteriophage having a surface polypeptide covalently linked to one site on a single stranded oligoribonucleotide, said oligoribonucleotide being linked via a second site to a matrix, and being characterized by a nucleic acid sequence complementary to a conserved region of a genome of a pathogenic organism;

b. a bacterial strain capable of becoming infected by the bacteriophage; and c. a ribonuclease capable of cleaving deoxyribonucleic acid-ribonucleic acid hybrids.

The invention is further embodied as a composition comprising a bacteriophage capable of infecting attenuated strains of Pseudomonas; a single stranded oligonucleotide; and a matrix, wherein a surface polypeptide of the bacteriophage is covalently linked to one site on the oligonucleotide and the matrix is linked to another site on the oligonucleotide, and the oligonucleotide is characterized by a nucleic acid sequence complementary to a conserved region of a genome of a pathogenic organism.

The invention further provides a method for quantitating a pathogenic organism in a biological fluid, the pathogenic organism being characterized by a single stranded genome having a restriction endonuclease recognition site near a conserved region of the genome, which method comprises:

a. combining the biological fluid with an oligonucleotide probe comprising a bacteriophage capable of infecting attenuated strains of Pseudomonas, said bacteriophage having a surface polypeptide covalently linked to one site on a single stranded oligonucleotide, said oligonucleotide being linked via a second site to a matrix and being characterized by a nucleic acid sequence complementary to the conserved region of the genome of the pathogenic organism and to one strand of the restriction endonuclease recognition site;

b. incubating the biological fluid and the oligonucleotide probe at a temperature and for a time sufficient to allow nucleic acid hybridization to occur, thereby forming a hybridization mixture;

c. incubating the hybridization mixture with a restriction endonuclease at a temperature and for a time sufficient to allow cleavage of all nucleic acids containing the restriction endonuclease recognition site, thereby releasing infective bacteriophage;

d. measuring the number of infective bacteriophage released in step c.

In another embodiment, the invention provides a kit comprising:

a. a bacteriophage capable of infecting attenuated strains of Pseudomonas, said bacteriophage having a surface polypeptide covalently linked to one site on a single stranded oligonucleotide, said oligonucleotide being linked via a second site to a matrix, and being characterized by a nucleic acid sequence complementary to a conserved region of a genome of a pathogenic organism and one strand of a restriction endonuclease recognition site;

b. a bacterial strain capable of becoming infected by the bacteriophage; and c. a restriction endonuclease capable of cleaving at the restriction endonuclease recognition site.

In another embodiment, the invention provides a method for quantitating a pathogenic organism in a biological fluid, the pathogenic organism being characterized by a double stranded genome, which method comprises:

a. combining the biological fluid with an oligoribonucleotide probe comprising a bacteriophage capable of infecting attenuated strains of Pseudomonas, said bacteriophage having a surface polypeptide covalently linked to one site on a single stranded oligoribonucleotide, said oligoribonucleotide being linked via a second site to a matrix and being characterized by a nucleic acid sequence complementary to the conserved region of the genome of the pathogenic organism;

b. incubating the biological fluid and the oligoribonucleotide probe at a temperature and for a time sufficient to allow nucleic acid hybridization to occur, thereby forming a hybridization mixture;

c. incubating the hybridization mixture with a ribonuclease at a temperature and for a time sufficient to allow cleavage of all deoxyribonucleic acid-ribonucleic acid hybrids, thereby releasing infective bacteriophage;

d. measuring the number of infective bacteriophage released in step c.

In another embodiment, the invention provides a kit comprising:

a. a bacteriophage capable of infecting attenuated strains of Pseudomonas, said bacteriophage having a surface polypeptide covalently linked to one site on a single stranded oligoribonucleotide, said oligoribonucleotide being linked via a second site to a matrix, and being characterized by a nucleic acid sequence complementary to a conserved region of a genome of a pathogenic organism;

b. a bacterial strain capable of becoming infected by the bacteriophage; and c. a ribonuclease capable of cleaving deoxyribonucleic acid-ribonucleic acid hybrids.

In yet another embodiment, the invention provides a composition comprising a bacteriophage capable of infecting attenuated strains of Salmonella; a single stranded oligonucleotide; and a matrix, wherein a surface polypeptide of the bacteriophage is covalently linked to one site on the oligonucleotide and the matrix is linked to another site on the oligonucleotide, and the oligonucleotide is characterized by a nucleic acid sequence complementary to a conserved region of a genome of a pathogenic organism.

In another embodiment, the invention provides a method for quantitating a pathogenic organism in a biological fluid, the pathogenic organism being characterized by a single stranded genome having a restriction endonuclease recognition site near a conserved region of the genome, which method comprises:

a. combining the biological fluid with an oligonucleotide probe comprising a bacteriophage capable of infecting attenuated strains of Salmonella, said bacteriophage having a surface polypeptide covalently linked to one site on a single stranded oligonucleotide, said oligonucleotide being linked via a second site to a matrix and being characterized by a nucleic acid sequence complementary to the conserved region of the genome of the pathogenic organism and to one strand of the restriction endonuclease recognition site;

b. incubating the biological fluid and the oligonucleotide probe at a temperature and for a time sufficient to allow nucleic acid hybridization to occur, thereby forming a hybridization mixture;

c. incubating the hybridization mixture with a restriction endonuclease at a temperature and for a time sufficient to allow cleavage of all nucleic acids containing the restriction endonuclease recognition site, thereby releasing infective bacteriophage;

d. measuring the number of infective bacteriophage released in step c.

In another embodiment, the invention provides a kit comprising:

a. a bacteriophage capable of infecting attenuated strains of Salmonella said bacteriophage having a surface polypeptide covalently linked to one site on a single stranded oligonucleotide, said oligonucleotide being linked via a second site to a matrix, and being characterized by a nucleic acid sequence complementary to a conserved region of a genome of a pathogenic organism and one strand of a restriction endonuclease recognition site;

b. a bacterial strain capable of becoming infected by the bacteriophage; and c. a restriction endonuclease capable of cleaving at the restriction endonuclease recognition site.

In another embodiment, the invention provides a method for quantitating a pathogenic organism in a biological fluid, the pathogenic organism being characterized by a double stranded genome, which method comprises:

a. combining the biological fluid with an oligoribonucleotide probe comprising a bacteriophage capable of infecting attenuated strains of Salmonella, said bacteriophage having a surface polypeptide covalently linked to one site on a single stranded oligoribonucleotide, said oligoribonucleotide being linked via a second site to a matrix and being characterized by a nucleic acid sequence complementary to the conserved region of the genome of the pathogenic organism;

b. incubating the biological fluid and the oligoribonucleotide probe at a temperature and for a time sufficient to allow nucleic acid hybridization to occur, thereby forming a hybridization mixture:

c. incubating the hybridization mixture with a ribonuclease at a temperature and for a time sufficient to allow cleavage of all deoxyribonucleic acid-ribonucleic acid hybrids, thereby releasing infective bacteriophage;

d. measuring the number of infective bacteriophage released in step c.

In another embodiment, the invention probides a kit comprising:

a. a bacteriophage capable of infecting attenuated strains of Salmonella, said bacteriophage having a surface polypeptide covalently linked to one site on a single stranded oligoribonucleotide, said oligoribonucleotide being linked via a second site to a matrix, and being characterized by a nucleic acid sequence complementary to a conserved region of a genome of a pathogenic organism;

b. an attenuated bacterial strain capable of becoming infected by the bacteriophage; and c. a ribonuclease capable of cleaving deoxyribonucleic acid ribonucleic acid hybrids.

DETAILED DESCRIPTION OF THE PREFERRED EMBODIMENTS

Figure 1:
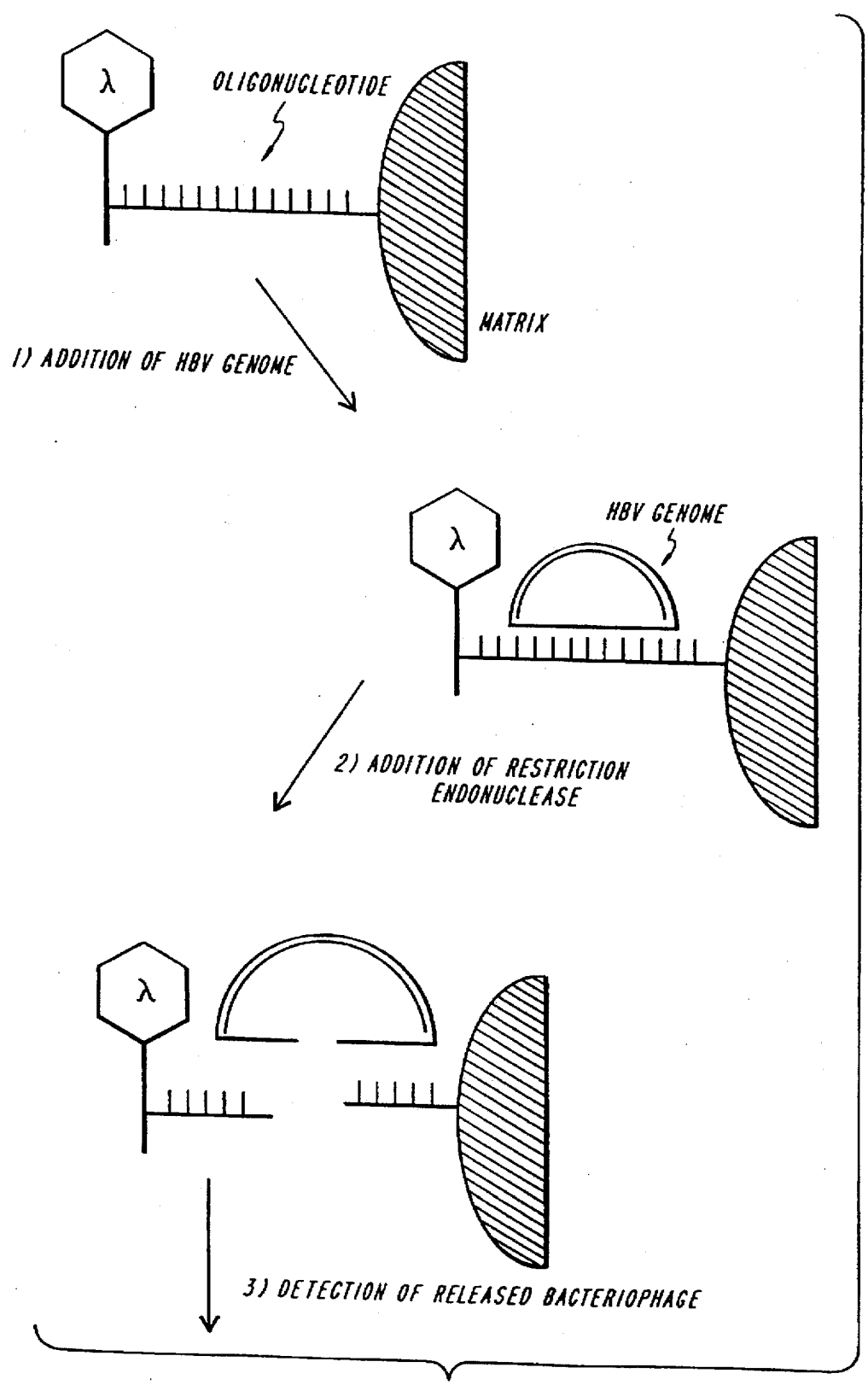
FIG. 1 shows a schematic depiction of the method of the invention.

Commonly assigned copending application Ser. No. 08/053,866, incorporated herein by reference, discloses an infective lambdoid bacteriophage having a modified tail protein which is chemically linked to a target molecule, in such a way that the target molecule is displayed on the outer surface of the bacteriophage tail. The target molecule of Ser. No. 08/053,866 may be embodied as a nucleic acid or as a substrate of an enzyme. Also disclosed in Ser. No. 08/053, 866 is a method of detecting a molecule of interest in a solution-to-be-tested, which method employs the above-described lambdoid bacteriophage. The molecule of interest in the method of Ser. No. 08/053,866 may be embodied as a nucleic acid, and the target molecule is processed in such a way that the bacteriophage is rendered reversibly non-infective. The non-infective bacteriophage is then treated with the solution-to-be-tested, and in the method of Ser. No. 08/053,866, the molecule of interest is capable of rendering the bacteriophage infective.

The composition of the present invention comprises a lambdoid bacteriophage, a single stranded oligonucleotide having a 5' terminus and a 3' terminus, and a matrix, a surface polypeptide of the bacteriophage being covalently linked to one terminus of the oligonucleotide and the matrix being linked to the other terminus of the oligonucleotide.

The oligonucleotide of the present invention is characterized by a nucleic acid sequence complementary to a conserved region of a genome of a pathogenic organism and to one strand of a restriction endonuclease recognition site. Stated in the terms of Ser. No. 08/053,866, the target molecule of the present invention is a nucleic acid, the oligonucleotide of the composition. The molecule of interest, the pathogen genome, is also a nucleic acid. The composition of the present invention differs from that of Ser. No. 08/053,866 in that the nucleic acid of the present invention is covalently attached to a matrix at another site on the nucleic acid which is not attached to the bacteriophage.

The method of the present invention differs from that of Ser. No. 08/053,866 in that the molecule of interest of the present invention is not itself capable of rendering the bacteriophage infective. Instead, hybridization of the target molecule to the molecule of interest in accordance with the method of the present invention generates a double stranded restriction endonuclease site, and treatment of the solution-of-interest with the appropriate restriction endonuclease renders the bacteriophage infective, thus allowing quantitation of the number of pathogen genomes present in the solution-of-interest.

Any pathogen genome may be quantitated using the compositions, methods, and kits of the present invention. Genomes comprising DNA or those comprising RNA, either double stranded or single stranded, may be quantitated using the compositions, methods, and kits of the present invention. Any viral genome may be quantitated using the compositions, methods, and kits of the present invention. For example, genomes of pox viruses, herpesviruses, adenoviruses, papova viruses, myxoviruses, retroviruses, arboviruses, picornaviruses, rabies viruses, rubella viruses, hepatitis viruses, and the like, may all be quantitated in accordance with the present invention. Similarly, any bacterial pathogen genome may be quantitated using the compositions, methods, and kits of the present invention. Genomes of both gram-positive and gram-negative bacteria may be quantitated in accordance with the invention. Genomes of bacterial species from any genus, such as Staphylococcus, Pneumococcus, Streptococcus, Bacillus, Corynebacterium, Listeria, Clostridium, Mycobacterium, Streptomyces, Nocardia, Pasteurella, Brucella, Haemophilus, Bordatella, Salmonella, Escherichia, Shigella, Vibrio, Borrelia, Leptospira, Mycoplasma, Chlamydia, Rickettsia, and the like, may all be quantitated using the compositions, methods, and kits of the present invention. Genomes of fungal pathogens may be quantiated in accordance with the present invention. Genomes of fungal species from any genus, for example Blastomyces, Cryptococcus, Candida, Coccidioides, Histoplasma, and the like, may all be quantitated using the compositions, methods, and kits of the present invention. Genomes of protozoal pathogens may also be quantitated in accordance with the present invention. Genomes of protozoal pathogens from any genus, such as Entamoeba, Giardia, Trichomonas, Trypanosoma, Leishmania, Plasmodium, Toxoplasma, and the like, may all be quantitated using the compositions, methods, and kits of the present invention. In short, any pathogenic organism which is shed into a biological fluid may be quantitated in accordance with the present invention. After processing which will allow for release of pathogen genomes, any tissue or organ in which a pathogen is sequestered may be subjected to quantitation using the compositions, methods, and kits of the present invention. If necessary, hydrolytic enzyme such as nucleases or proteases will be inactivated, for example, by heating, in order to avoid subsequent interference with the assay system.

As defined herein, an oligonucleotide probe of the invention comprises a bacteriophage which is covalently linked to a functional group present on a first nucleic acid residue of an oligonucleotide, the oligonucleotide being linked via a second functional group present on a second nucleic acid residue of the oligonucleotide to a matrix. Any two nucleic acid residues present on the oligonucleotide may serve as linkage sites between the oligonucleotide, the bacteriophage, and the matrix, so long as the availability of the oligonucleotide for hybridization to the pathogen genome is preserved, and so long as no steric hindrance occurs between the bacteriophage and the matrix. In one preferred form, the bacteriophage is linked to the oligonucleotide via one terminal nucleic acid residue and the matrix is linked to the oligonucleotide via the other terminal nucleic acid residue. The oligonucleotide moiety of the oligonucleotide probe of the invention is characterized by a nucleic acid sequence complementary to a conserved region of a genome of a pathogenic organism, and in one preferred embodiment, is also complementary to one strand of a restriction endonuclease recognition site. Preferably, the oligonucleotide moiety of the oligonucleotide probe of the invention is complementary to about ten to about fifty nucleotides of a conserved region of a genome of a pathogenic organism. More preferably, the oligonucleotide moiety of the oligonucleotide probe of the invention is complementary to about fifteen to about thirty nucleotides of a conserved region of a genome of a pathogenic organism. In accordance with the present invention, the oligonucleotide moiety of the oligonucleotide probe may be an oligodeoxyribonucleotide, an oligoribonucleotide, or a hybrid oligonucleotide having both ribonucleotide and deoxyribonucleotide components. When the oligonucleotide moiety of the oligonucleotide probe of the invention is embodied as an oligoribonucleotide, it is not necessary that the nucleic acid sequence of the oligonucleotide moiety be complementary to one strand of a restriction endonuclease recognition site. In the oligoribonucleotide moiety embodiment, the oligonucleotide probe of the invention is characterized by a nucleic acid sequence complementary to a conserved region of a genome of a pathogenic organism.

As set forth above, the oligonucleotide probe of the present invention is designed as a molecule complementary to a conserved region of a pathogen genome. Preferably, the region of pathogen genome chosen to design the oligonucleotide probe is unique for the pathogen. Any portion of a region of a genome which is conserved among the subspecies of a pathogenic organism may serve as a template for the oligonucleotide moiety of the oligonucleotide probe of the invention, so long as a sufficient number of consecutive conserved nucleotides are present to allow hybridization to occur between the oligonucleotide probe and the pathogen genome. Identification of conserved, unique regions of pathogen genomes is within the level of skill in the art, since many pathogen genomes are known or are readily determinable, and conserved regions of such genomes are readily apparent by comparison with other pathogen genomes. In accordance with the invention, the pathogen genome may be embodied as a single stranded or double stranded DNA genome, an RNA genome, or as mRNA.

In one embodiment, the oligonucleotide moiety of the oligonucleotide probe of the invention also contains one strand of a restriction endonuclease recognition and cleavage site, so that binding of the pathogen genome to the oligonucleotide completes the restriction endonuclease cleavage site. Many restriction endonuclease cleavage sites are known, and the presence of such sites in a pathogen genome can be readily identified, for example, by consultation with the catalogues of vendors of restriction endonucleases such as New England Biolabs, Inc. Preferably, the restriction endonuclease recognition and cleavage site chosen for designing the oligonucleotide will be in the vicinity of the conserved region of the pathogen genome. More preferably, the restriction endonuclease recognition and cleavage site chosen for designing the oligonucleotide will be within the conserved region of the pathogen genome.

For example, several oligonucleotides suitable for use in an assay to detect HBV in accordance with the present invention may be identified as follows. The sequences of seven different HBV major subtypes are known. Inspection of the sequences reveals three stretches of at least 17 bases in the single-stranded region of the HBV genome that are conserved among the seven subtypes and that span a restriction endonuclease cleavage recognition site. The sequence set forth in SEQ ID NO:1 corresponds to a conserved region, nucleotides 244 through 288 of the HBV. One strand of an XbaI cleavage recognition site is present at nucleotides 6 through 11 of SEQ ID NO:1. The sequence set forth in SEQ ID NO:2 corresponds to a second conserved region, nucleotides 169 through 191 of the HBV. One strand of an AvrII cleavage recognition site is present at nucleotides 12 through 17 of SEQ ID NO:2. The sequence set forth in SEQ ID NO:3 corresponds to a third conserved region, nucleotides 1410 through 1426 of the HBV. One strand of an AatII cleavage recognition site is present at nucleotides 6 through 11 of SEQ ID NO:3.

In addition to assaying DNA viruses containing partially single stranded DNA genomes, the method of this invention is also applicable to detect double stranded DNA genomes such as that of human cytomegalovirus (CMV). When the composition, methods, or kits of the invention are used to detect double-stranded DNA genomes, either strand of the genome may be detected. Thus, in this embodiment, the oligonucleotide moiety of the oligonucleotide probe may either be the coding strand of the pathogen genome or its complement. Although some subtypes of CMV have not yet been sequenced, it is possible to detect most CMV subtypes in accordance with the present invention by employing two or more different oligonucleotides from genes present on all CMV genomes. When employing more than one oligonucleotide, it is preferable that the same restriction endonuclease cleavage site be present in each oligonucleotide. For example, the DNA sequences encoding two human CMV phosphoproteins, pp 65 and pp 71, are known, as well as the location of several restriction endonuclease cleavage sites (Rüger et al. (1987) *J. Virol.* 61:446–453). SEQ ID NO:4 corresponds to nucleotides 1190 to 1209 of the human CMV pp 65 gene, and SEQ ID NO:5 corresponds to nucleotides 1307 to 1326 of the human CMV pp 65 and pp 71 combined sequence. One strand of the BglII restriction endonuclease recognition site is present at nucleotides 8 to 13 of SEQ ID NO:4 and at nucleotides 8 to 13 of SEQ ID NO:5.

The method of the invention can also be applied to organisms containing RNA genomes. For such organisms, a region of the RNA may (but not necessarily) first be copied to form a complementary DNA, or copy DNA (cDNA), in order for the genome to be detected in accordance with the invention. This is typically accomplished using the enzyme reverse transcriptase. Other enzymes capable of transcribing cDNA from mRNA would also be suitable for performing this reaction. The hepatitis C virus (HCV) is an example of an organism with an RNA genome. The most conserved region of the viral genome among HCV subtypes is the noncoding region which is 5' to the transcription initiation site (Chen et al., *Virology* 188:102–113 (1992)). For example, an oligonucleotide complementary to the sequence spanning nucleotides −71 through −51 of the HCV genome (SEQ ID NO:7) may be employed as a primer for reverse transcriptase. The resulting cDNA contains a Sma I restriction endonuclease cleavage site. An oligodeoxyribonucleotide identical to the 21 nucleotide sequence of the HCV genome, nucleotides −202 through −222 (set forth in SEQ ID NO:8) which spans the SmaI site, may also be a component of the oligonucleotide probe of the invention.

Alternatively, a restriction endonuclease recognition and cleavage site may be constructed on the oligonucleotide probe of the invention in such a way that binding of the oligonucleotide completes a recognition and cleavage site more distal from the conserved region of the pathogen genome. In this embodiment, the more distal restriction endonuclease recognition and cleavage site is identified on the pathogen genome, and a determination is made regarding the optimal number of residues of the conserved region of the pathogen genome which must be present in order for specific binding to occur. Such identifications and determinations are within the level of skill in the art.

In accordance with the invention, the oligonucleotide moiety of the oligonucleotide probe is modified to permit covalent or non-covalent linkage to a solid support or matrix at one functional group present on a first nucleic acid residue or site of the oligonucleotide. The oligonucleotide moiety may be covalently or non-covalently linked to the solid support or matrix at any site, so long as linkage with the bacteriophage at another nucleic acid residue or site is allowed while maintaining the availability of the oligonucleotide moiety for hybridization to the pathogen genome. The oligonucleotide moiety is further modified to permit covalent linkage to a bacteriophage via a functional group present on a second nucleic acid residue of the oligonucleotide, as described above. Preferably, the oligonucleotide moiety is linked to the bacteriophage either at its 5' terminus or at its 3' terminus, so long as linkage with the solid support or matrix at the other terminus is allowed. Preferably, the oligonucleotide moiety of the oligonucleotide probe has a primary amino group present at its 5' terminus for linkage to the matrix, and a sulfhydryl group present at its 3' terminus for linkage to the bacteriophage.

Any chemical portion Of the oligonucleotide moiety may be modified within the oligonucleotide probe of the invention, so long as the oligonucleotide probe's ability to hybridize to the pathogen genome is preserved. For example, the nucleotides of the oligonucleotide moiety may be linked via other than phosphodiester internucleoside linkages known in the art such as phosphorothioates, phosphorodithioates, phosphoramidates, carbamates, carbonates, phosphate esters, alkylphosphonates, alkylphosphonothioates, phosphoramidites, phosphate esters, acetamidates, carboxymethyl esters, carbonates, phosphate triesters, or the like. Alternatively, the nucleic acid base of the 3' terminus may be modified to include a sulfhydryl group, or the sugar moiety of the 3' terminus may be modified to contain a sulfhydryl group. The 5' terminus of the oligonucleotide may be modified so that the primary amino group is present on the phosphodiester backbone, the nucleic acid base or on the sugar. In addition, the sugar of any ribonucleotide in the oligonucleotide probe may be modified by having an arabinose instead of a ribose, or having a 2'-substitution such as a 2'-O-alkyl, 2'-O-aryl, 2'-O-allyl, 2'-halo, or 2'-amino substitution. Methods for preparing such modifications of nucleic acids are well known in the art, as set forth, for example, in Uhlmann et al., (1990) *Chem. Rev.* 90, 543–584, in Protocols for Oligonucleotides and Analogs, Methods in Molecular Biology, vol. 20, S. Agrawal, ed. (Humana Press, Totowa, N.J. 1993) and in Protocols for Oligonucleotide Conjugates, Methods in Molecular Biology, vol. 26, S. Agrawal, ed. (Humana Press, Totowa, N.J. 1993).

As a specific example of such modifications, the oligonucleotide of SEQ ID NO:1 may be designed with the thiol-containing compound 6-mercaptohexanol linked at the 3' position of the 3' terminal sugar of the oligonucleotide and the amino-containing compound 6-aminohexanol linked to the 5' phosphate at the 5' end of the oligonucleotide. Such modified oligonucleotides are also commercially available, for example, from Integrated DNA Technologies, Inc., Coralville, Iowa.

In addition to the 5' and 3' termini of the oligonucleotide, modifications can occur at internal bases and sugars and on the phosphodiester backbone at positions other than the 5' terminal phosphate, so long as the oligonucleotide probe's ability to hybridize to the pathogen genome is preserved. For example, phosphorothioate diesters can be incorporated into the phosphate backbone of the oligonucleotide at any position. Phosphothioate diesters can by alkylated with reagents containing γ-bromo-α,β-unsaturated carbonyls, iodo- or bromo-acetamides, or aziridinylsulphonamides to produce phosphorothioate triesters (Conway et al. (1991) in *Oligonucleotides and Analogues: A practical approach*, Eckstein (ed.), Oxford University), Press, New York, pp. 211–239). In another example, modified pyrimidine nucleosides can be incorporated into the oligonucleotide. Such modifications include modifications of the C-5 position of 2'-deoxyuridine and modifications of the $N^4$ of 2'-deoxycytodine, as described by Ruth (1991) in *Oligonucleotides and Analogues: A practical approach*, Eckstein (ed.), Oxford University Press, New York, pp. 255–282.

Any solid support is suitable as a matrix in accordance with the present invention. For example, polypropylene, resins, polystyrene, and the like are suitable as matrix components of the composition of the invention. Any membrane designed for covalent or non-covalent attachment of molecules through primary amino groups is also suitable as a matrix in accordance with the present invention. One suitable membrane is the Immobilon™ AV affinity membrane available from Millipore (Bedford, Mass.). Microtiter plates of any material are also suitable matrix components of the composition of the invention. Methods are known for covalent and non-covalent attachment of free oligonucleotides to a variety of solid supports, for example, as set forth in EP 439,222 and EP 455,905. In accordance with the invention, the oligonucleotide probe may be attached directly to the matrix, or it may be attached to a linking molecule which is in turn attached directly to the matrix. In accordance with the invention, the oligonucleotide may be attached covalently or non-covalently to the linking molecule. Any linking molecule is suitable to attach the oligonucleotide probe to the matrix, so long as the linking molecule can maintain an attachment between the oligonucleotide and the matrix which is maintained during hybridization of the oligonucleotide probe to the pathogen genome. For example, avidin or streptavidin can be covalently attached to the matrix (such streptavidin-containing matrices are commercially available, e.g., Reacti-Bind™, Pierce, Rockford, Ill.) to serve as a linking molecule which will bind biotinylated oligonucleotides. Alternatively, the oligonucleotide may be covalently attached to the matrix, for example, through a thiol group incorporated in the oligonucleotide. One such example has been described by Blanks and McLaughlin (1991) in *Oligonucleotides and Analogues: A practical approach*, Eckstein (ed.), Oxford University Press, New York, pp. 241–254.

Any bacteriophage is suitable for covalent linkage to the oligonucleotide of the composition of the invention. Preferably, bacteriophage which infect either *Bacillus subtilis*, *Lactococcus lactis*, attenuated strains of Pseudomonas, attenuated strains of Salmonella, or attenuated strains of *Escherichia coli* may be employed.

Examples of preferred bacteriophage that infect *Bacillus subtilis* are φ29, PZA, SP01 and SP82 and any derivatives thereof. Examples of preferred bacteriophage that infect *Lactococcus lactis* are φvLM3 and φLC3 and any derivatives thereof. Examples of preferred bacteriophage that infect Pseudomonas are φCTX and Pf3 and any derivatives thereof. Examples of preferred bacteriophage that infect Salmonella are P22 and PSP3 and any derivatives thereof. Examples of preferred bacteriophage that infect *Escherichia coli* are the T-even phages, T3, T7, single stranded DNA phages, RNA phages, lambdoid phages and any derivatives thereof.

More preferably, φ29, φLC3, φCTX, P22, T4 (a T-even phage), φX174 (a single-stranded DNA phage), R17 (an RNA phage), T7 or a lambdoid phage may be employed. Most preferably, the lambdoid phages λ, λvir, φ80, φ81, phage 21, phage 82, phage 424, phage 432, λimm434, λEMBL derivatives, and λgt derivatives are all suitable for use in the oligonucleotide probe of the invention.

In accordance with the invention, the covalent linkage between the bacteriophage and the oligonucleotide occurs via any polypeptide present on the surface of the bacteriophage so long as the infectivity of the bacteriophage is not diminished. For example, any of the polypeptides present on the surface of the head of the bacteriophage, or any of the polypeptides present on the surface of the tail of the bacteriophage may act as the sites of linkage between the bacteriophage and the oligonucleotide. When a lambdoid bacteriophage is used in the oligonucleotide probe of the invention, either of the two major head proteins of bacteriophage λ, gpD and gpE, or the major tail protein of bacteriophage λ, gpV, may serve as the specific site of linkage between the bacteriophage and the oligonucleotide. Similarly, polypeptides analogous to the bacteriophage λ proteins, which are present on other bacteriophages, may also act as the sites of linkage between the bacteriophage and the oligonucleotide. Alternatively, a modified bacteriophage λ gpV protein, or a modified version of an analogous tail protein from another bacteriophage, may serve as the site of linkage between the bacteriophage and the oligonucleotide. Examples of sites for attachment of oligonucleotides to bacteriophage other than λ are: gp9 (tail protein) or gp5 (head protein) of P22, and gp8 (major capsid protein) of φ29.

The specific protein to which the oligonucleotide is to be attached need not be identified since any protein present on the surface of the bacteriophage can act as the site of linkage, so long as the infectivity of the bacteriophage is not diminished. Preferably, linkage to the oligonucleotide occurs via a sulfhydryl group on the bacteriophage surface polypeptide. More preferably, the linkage to the oligonucleotide occurs via a cysteine residue on the bacteriophage surface polypeptide. The suitability of a particular sulfhydryl residue for oligonucleotide attachment may be assessed as follows. Bacteriophage are exposed to a chemical capable of reacting with sulfhydryl groups for a time and at a temperature sufficient to allow modification of any sulfhydryl groups that may be present on the surface of the bacteriophage. Such chemicals include, without limitation, N-(7-dimethylamino-4-methylcoumarinyl)-maleimide; 5,5'-dithiobis(2-nitrobenzoic acid); 3-(N-maleimidopropionyl)-biocytin, and the like. Specific protocols for labeling protein sulfhydryl groups with these chemicals and for analyzing proteins thus modified are described, for example, in Yamamoto, et al., *Anal. Biochem.* (1978) 84, 313–318; Zelakowski, *Anal. Biochem* (1980) 103, 307–312; and Bayer et al., *Methods Enzymol.* (1990) 184, 138–160. Titers of modified and unmodified bacteriophage may be compared in order to determine whether the modification of the sulfhydryl group affects infectivity of the bacteriophage. Methods for titering bacteriophage vary somewhat depending on the specific bacteriophage employed, and such methods are well-known in the art. For example, when a lambdoid bacteriophage is used, the pSYM1 plasmid disclosed in Ser. No. 08/053,866 may be used to produce a modified bacteriophage λ gpV protein in which the C-terminal serine has been replaced with a cysteine. The modified gpV protein may be incorporated into a lambdoid bacteriophage using known methods, as set forth in detail in Ser. No. 08/053,866. The lysate containing the modified bacteriophage may be purified using known methods, and the bacteriophage having the modified gpV polypeptide on their surfaces may be linked to a sulfhydryl group of the oligonucleotide of the present invention.

As set forth above, the composition of the invention comprises the oligonucleotide moiety covalently linked at one terminus to a lambdoid bacteriophage and covalently or non-covalently linked at the other terminus to a matrix. To maintain the sensitivity of the method of the invention it is necessary that each bacteriophage be linked to only one oligonucleotide moiety. Random attachment of the oligonucleotide to the bacteriophage using glutaraldehyde is not suitable for making the composition of the invention, since such random attachment does not allow control of the number of linkage sites.

With the above restrictions in mind, any cross-linking agent that allows controlled modification of the surface polypeptides may be employed to form the bacteriophage-oligonucleotide linkage found in the composition of the invention. Preferably, the functional group of the cross-linking reagent that reacts with the bacteriophage is one that reacts with amines or with sulfhydryl groups. Several different bifunctional cross-linking reagents can be employed to effect covalent attachment of the oligonucleotide to the bacteriophage. Preferably, a cross-linking reagent is used which reacts with amines is used. More preferably, a cross-linking reagent which reacts with sulfhydryl groups is used, since there are relatively few free sulfhydryl groups present on the surface of lambdoid bacteriophage. Specific cross-linking reagents suitable for forming the bacteriophage-oligonucleotide linkage are, for example, bismaleimidohexane, succinimidyl-4-(N-maleimidomethyl) cyclohexane-1-carboxylate, disuccinimidyl suberate, and the like.

The oligonucleotide probe of the invention may be made by first attaching the bacteriophage to the oligonucleotide moiety to form a bacteriophage-oligonucleotide complex, followed by attachment of the bacteriophage-oligonucleotide complex to the matrix. Any method may be employed to attach the oligonucleotide moiety to the bacteriophage, so long as the method allows attachment of preferably only one oligonucleotide per bacteriophage, and so long as infectivity of the bacteriophage is not irreversibly destroyed. Attachment of more than one oligonucleotide moiety to the bacteriophage will obscure the detection of some of the pathogen genomes, thereby resulting in a corresponding underestimate of the number of pathogens present. Urdea et al. (*Nucleic Acids Res.* 16: 4937–4956, 1988) describe methods for covalently attaching the protein enzymes horseradish peroxidase and alkaline phosphatase to $N^4$-alkylamino deoxycytidine-containing oligodeoxyribonucleotides. In general, any heterobifunctional cross-linker or homobifunctional cross-linker such as those available from Pierce (Rockford, Ill.) can be employed to cross-link a protein to an oligonucleotide containing a functional group which reacts with the cross-linking reagent. In the aforementioned example, the $N^4$-alkyamino group reacts with the cross-linking reagent, diisothiocyanate. Generally, the method of attachment of the oligonucleotide moiety to the bacteriophage will employ a large excess of the number of bacteriophage over the number of oligonucleotide molecules. In accordance with the invention, bacteriophage having oligonucleotide attached thereto are separated from bacteriophage which do not have oligonucleotide attached thereto, and from oligonucleotides that are not linked to both the bacteriophage and the solid-support matrix.

More preferably, the oligonucleotide probe of the invention may be made by first attaching the oligonucleotide moiety to the matrix to form an oligonucleotide-matrix complex, followed by attachment of the oligonucleotide-matrix to the bacteriophage. When the oligonucleotide probe of the invention is made in this way, in order to ensure that each bacteriophage is tethered by only one oligonucleotide, the oligonucleotide moieties on the matrix must be separated by approximately the distance of the length of a bacteriophage plus the length of two oligonucleotide moieties. Methods for determining how far apart the oligonucleotide moieties should be for an oligonucleotide of a particular length and for a particular bacteriophage on the matrix are known.

For example, for a 45-mer oligonucleotide moiety to be attached to bacteriophage λ, the oligonucleotide moieties on the matrix must be separated by about 260 nm, since bacteriophage λ is 230 nm in length and a 45-mer oligonucleotide is approximately 15 nm in length. A mean separation ±3 standard deviations (calculated using a Poisson distribution) includes 99.74% of the oligonucleotides, therefore, a mean separation of 313 nm (mean−3×√mean= 260 nm) is sufficient to ensure that greater than 99.74% of the phage are tethered by only one oligonucleotide.

The density of oligonucleotides bound to matrix can be controlled by the concentration of oligonucleotide employed and by the duration of binding reaction. At lower concentrations, it takes longer to bind a specific percentage of the total oligonucleotide present than at higher concentrations. To establish the optimal conditions for a particular application, radiolabeled oligonucleotides may be employed and the amount of radiolabel bound to the filter can be determined using well-known methods. When the oligonucleotide is a 45-mer and the bacteriophage is λ as set forth above, to ensure a sufficient distance between oligonucleotide molecules, the preferred maximum acceptable number of oligonucleotide molecules bound to the membrane may be determined using the assumption that each oligonucleotide is in the center of a circle with a radius of 313 nm and thus occupies $3.1 \times 10^{-13}$ $M^2$. For example, a 1 cm² membrane will preferably contain no more than approximately $3 \times 10^8$ oligonucleotide molecules.

Employing the calculations set forth above to an oligonucleotide probe comprising bacteriophage T4, which is 310 nm long, results in each bacteriophage occupying $5.0 \times 10^{-13}$ $M^2$. Thus, a 1 cm² membrane will preferably contain no more than approximately 2×10⁸ oligonucleotide molecules when bacteriophage T4 is to be employed.

The Immobilon™ AV affinity membrane described above is particularly suitable as a matrix for making the composition of the invention by first attaching the oligonucleotide moiety to the matrix. Commercially available solid support matrices of porous glass, having the initial nucleotide residue bound thereto, are not suitable for this method of making the composition of the invention, since the porous glass does not provide sufficient access to the oligonucleotide by the lambdoid bacteriophage in the subsequent linkage step.

After binding the oligonucleotides, the remaining reactive groups of the membrane may be inactivated by reacting the membrane with 10% ethanolamine in 1M sodium bicarbonate, pH 9.5 for two hours at 25° C. The membrane is then washed with 0.5M potassium phosphate, pH 7.5. An excess of bacteriophage is then combined with the oligonucleotide-matrix complex, to ensure that essentially all of the bound nucleotides are attached to a bacteriophage. In accordance with the invention, controls are performed during the attachment of bacteriophage to the solid-support matrix via the oligonucleotide and not some other residue on the bacteriophage. For use in the method of the invention or in the kit of the invention, the membrane oligonucleotide probe described above may be cut into strips and the number of bacteriophage on each strip may be determined.

The method of detection is depicted in FIG. 1. In accordance with method of the invention, the oligonucleotide probe of the invention is combined with a sample of a biological fluid which may contain a pathogenic organism. Any biological fluid may be assayed using the method of the invention. As defined herein, a biological fluid may be serum, plasma, whole blood, urine, saliva, sputum, milk, lymphatic fluid, lacrimal secretions, cerebrospinal fluid, bone marrow, ascites, cell lysate, biopsy homogenate, culture supernatant, sewage, and the like. The biological fluid sample may be assayed neat or diluted, or it may be processed to expose nucleic acids, for example, by heating or by incubating the biological fluid sample with a nucleic acid strand-separating reagent. Methods for processing biological fluids to expose nucleic acids are known.

In accordance with the method of the invention, the biological fluid sample and the oligonucleotide probe are incubated at a temperature and for a time sufficient to allow nucleic acid hybridization to occur, thereby forming a hybridization mixture. Generally, incubation conditions for nucleic acid hybridization are well known, requiring relatively high temperatures and high salt concentrations, for example, for "stringent" hybridization. Because of the need to avoid irreversibly destroying the infectivity of the lambdoid bacteriophage moiety of the probe, the hybridization incubation conditions may be modified by addition of appropriate salts or by addition of polyamines, or the like, to allow hybridization to proceed efficiently at less than optimal hybridization temperatures. Additionally, the restriction endonucleases require 10 mM $Mg^{++}$; this concentration of $Mg^{++}$ also is required to maintain bacteriophage viability. Finally, the pH of the hybridization buffer is important for optimal restriction endonuclease cleavage, stability of the hybrid, and viability of the bacteriophage. A preferred range is from pH 7.0 to 8.0. Such determinations of optimal hybridization conditions are routine for those of skill in the art.

The nature of the restriction endonuclease to be employed must be considered in determining the conditions for hybridization since the enzyme must be active under the conditions employed. The activities of several restriction endonucleases are very dependent on salt concentrations. Restriction endonucleases such as SacI, XmaI and KpnI are optimal in no salt, whereas StyI, EagI and BglI are more active in 100 mM NaCl. Also, some restriction endonucleases require lower temperatures such as ApaI, AgeI and SmaI, which function best at 25° C. In contrast, BstEII, TaqI and Tth111I function best between 60° C. and 65° C. Most restriction endonucleases, such as XbaI, function optimally at 37° C. Optimal conditions for restriction endonucleases may be found in catalogues distributed by vendors, such as New England Biolabs (Beverly, Mass.) and Boehringer Mannheim (Indianapolis, Ind.), that supply such enzymes.

For example, Wahl, et al. (*Methods Enzym.* 152:399–407, 1987) provide the formula, $T_m=81.5+16.6(\log_{10}[Na^+])+41$ (fraction G+C)−(500/N), for estimating the melting temperature, $T_m$, for oligonucleotides of length N, at known salt concentrations. As indicated in this formula, raising the salt concentration results in a rise in the $T_m$. To hybridize oligonucleotides, it is preferable to work at 5° C. to 10° C., or more, below the $T_m$, and it is most preferable to work at 10° C., or more, below the $T_m$. To find the minimal length of homology the formula for calculating $T_m$ must be rearranged to solve for N, $N=500/[81.5+16.6(\log_{10}[Na^+])+41$ (fraction G+C)−$T_m$]. The 45-mer set forth in SEQ ID NO:1 contains 22 G+C's, and the XbaI buffer (or hybridization buffer) contains 0.05M $Na^+$, thus with a $T_m=47°$, N=15. Thus, the most preferred oligonucleotide to employ contains 15 or more bases. Therefore, the entire 45-mer set forth in SEQ ID NO:1 is not essential, and the preferred oligonucleotide moiety for construction of an oligonucleotide probe for HBV would be a subsequence of SEQ ID NO:1 such as the 20-mer set forth in SEQ ID NO:6.

In accordance with the method of the invention, after a time sufficient to allow substantially all of the pathogen genomes present in the biological fluid to hybridize to the oligonucleotide probe, the hybridization mixture is combined with the appropriate restriction endonuclease, at a temperature and for a time sufficient to allow cleavage of all nucleic acids containing the restriction endonuclease recognition site, thereby releasing infective bacteriophage. Such incubation conditions are known for commercially available restriction endonucleases, and they are readily determinable for other restriction endonucleases. When the oligonucleotide moiety of the oligonucleotide probe is an oligoribonucleotide, the hybridization mixture is combined with a suitable nucleolytic enzyme capable of cleaving DNA-RNA hybrids, at a temperature and for a time sufficient to allow cleavage of all DNA/RNA duplexes. Such incubation conditions are readily determinable for nucleolytic enzymes.

The number of infective bacteriophage released from the matrix by the action of the restriction endonuclease may be determined using known methods, for example, by incubating the sample of biological fluid with an aliquot of a suitable bacterial host for a time sufficient to allow infection by the released bacteriophage, plating the bacterial culture thus formed, and by counting the number of plaques formed on the resulting lawn of bacteria. Any bacterial host is suitable for performing this step of the method of the invention, so long as the host is not restricted for growth of the bacteriophage moiety of the oligonucleotide probe of the invention. Alternatively, a polyclonal antiserum specific for the bacteriophage used in the method employed in an ELISA type assay to detect the released bacteriophage. Other detection methods, such as colorimetric or luminescent assay for release of *E. coli* cytoplasmic enzymes, may also be used to quantify the number of infective lambdoid bacteriophage released from the matrix.

For detection of pathogenic organism characterized by RNA genomes, such as HCV, a processing step, treatment of the sample of biological fluid with reverse transcriptase, is performed prior to combining the sample with the oligonucleotide probe in order to produce cDNA capable of binding to the oligonucleotide probe. Similarly, for detection of pathogens characterized by a double-stranded DNA genome using the method of the invention, a processing step is performed prior to combining the sample with the oligonucleotide probe. In this processing step, a region of the genome's double helix is exposed to the oligonucleotide probe, for example, by restriction endonuclease digestion of the genome. The restriction endonuclease chosen to digest the double stranded genome is one which will provide restriction fragments containing the conserved region of the pathogen genome, preferably restriction fragments containing the conserved region at a site which is easily rendered single-stranded. An oligonucleotide probe of the invention containing an oligoribonucleotide moiety is particularly suitable for quantitation of pathogens characterized by a double stranded genome. Since RNA/DNA hybrids are more stable than DNA/DNA hybrids, processing steps performed prior to combining the sample with the oligonucleotide probe that would unwind the DNA helix would permit the RNA/DNA hybrid to form.

Figure 2:
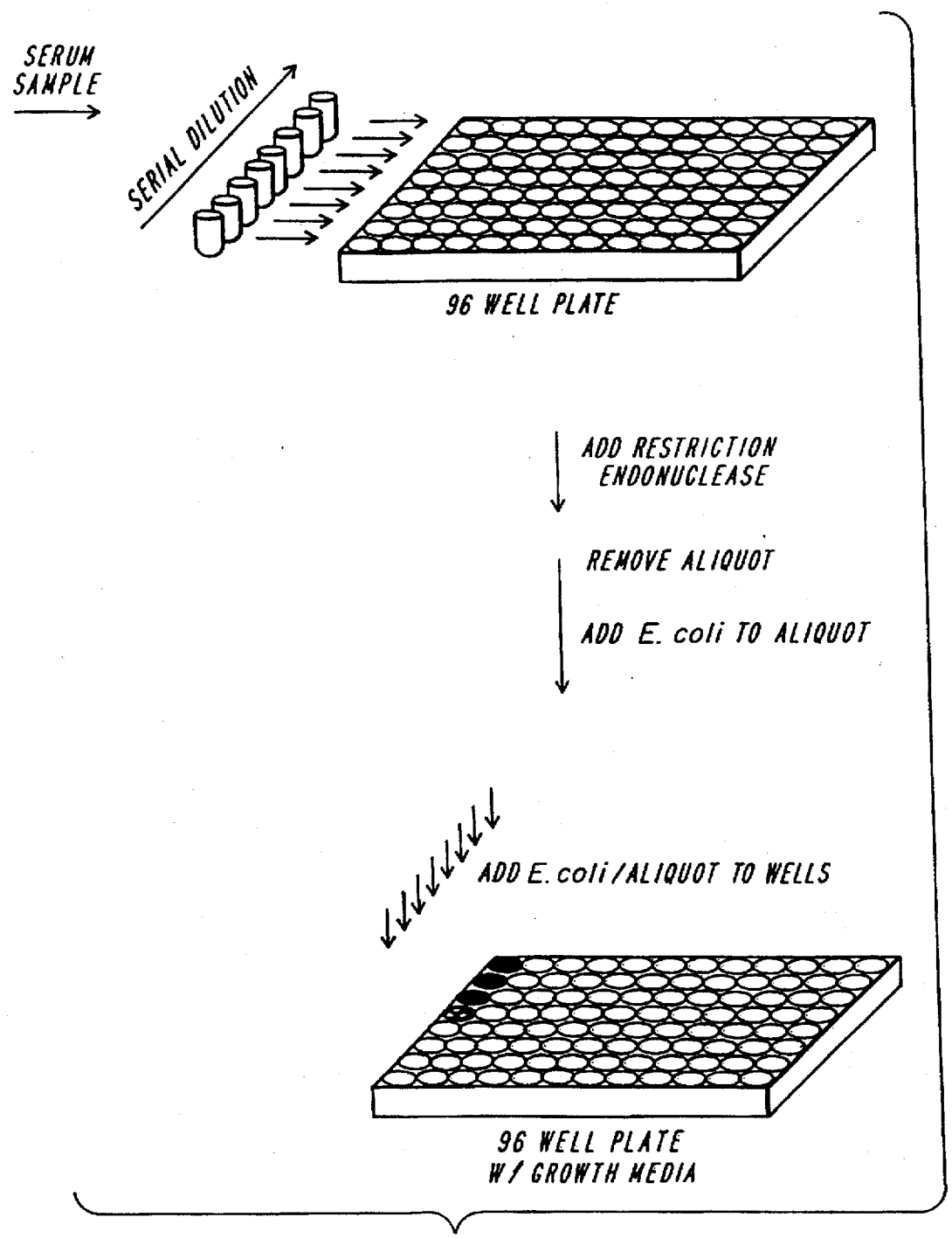
FIG. 2 shows an exemplary automated system for performing the method of the invention.

The method of the invention may be performed manually, or it may be automated, for example, as set forth in FIG. 2. In the automated embodiment of the method of the invention, the oligonucleotide probe is bound to polystyrene wells of a microtiter plate using known methods. For example, attachment of the oligonucleotide probe to the microtiter plate may be performed using a plate coating system, such as the Dynatech Autoprocessor (Dynatech Laboratories, Inc., Chantilly, Va.).

The present invention may also be embodied as a kit for detection and quantitation of a pathogenic organism in a biological fluid. The kit of the invention includes the oligonucleotide probe composition described above, along with such other components as allow practice of the method of the invention. For example, buffers for enhancing the hybridization reaction of the method of the invention may be provided as kit components. A restriction endonuclease capable of cleaving the oligonucleotide moiety of the oligonucleotide probe may also be provided as a kit component. When the oligonucleotide moiety is an oligoribonucleotide, a suitable nucleolytic enzyme capable of cleaving DNA-RNA hybrids may be provided as a kit component. Buffers suitable for the enzyme reactions employed in the method may also be included in the kit of the invention. When the number of bacteriophage released from the matrix is measured using a bacterial host strain, a bacterial host capable of becoming infected by the particular bacteriophage contained in the oligonucleotide probe may also be provided as a kit component. When the number of bacteriophage released from the matrix in accordance with the method of the invention is measured using a polyclonal antiserum, a polyclonal antiserum capable of specifically reacting with the bacteriophage moiety of the oligonucleotide probe may be provided as a kit component. In this embodiment, reagents suitable for detecting the polyclonal antibody may also be provided as kit components. When colorimetric or luminescent methods are used to detect the number of bacteriophage released from the matrix, reagents suitable for performing the colorimetric or luminescent methods such as enzymes or substrates may be included as kit components. Additional kit components may also be included which enhance the convenience of the assay, for example, assay tubes, pipette tips, Petri dishes, agar, and the like.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefore intended to be embraced therein.

---

We claim:

1. A method for quantitating a pathogenic organism in a biological fluid, the pathogenic organism being characterized by a double stranded deoxyribonucleic acid genome, which method comprises:
   a) processing the biological fluid to release the genome of the pathogen;
   b) combining the biological fluid with an oligoribonucleotide probe comprising a lambdoid bacteriophage having a surface polypeptide covalently linked to one site on a single stranded oligoribonucleotide, said oligoribonucleotide being linked via a second site to a matrix and being characterized by a nucleic acid sequence complementary to a conserved region of the genome of the pathogenic organism;
   c) incubating the biological fluid and the oligoribonucleotide probe at a temperature and for a time sufficient to allow nucleic acid hybridization to occur without irreversibly destroying the infectivity of the lambdoid bacteriophage, thereby forming a hybridization mixture;
   d) incubating the hybridization mixture with a ribonuclease at a temperature and for a time sufficient to allow cleavage of all deoxyribonucleic acid-ribonucleic acid hybrids, thereby releasing infective lambdoid bacteriophage;
   e) measuring the number of infective lambdoid bacteriophage released in step d, wherein the number of infective lambdoid bacteriophage released corresponds to the number of pathogen genomes present in the biological fluid.

2. A method for quantitating a pathogenic organism in a biological fluid, the pathogenic organism being characterized by a double stranded deoxyribonucleic acid genome, which method comprises:
   a) processing the biological fluid to release the genome of the pathogen;
   b) combining the biological fluid with an oligoribonucleotide probe comprising a bacteriophage capable of infecting *Bacillus subtilis*, said bacteriophage having a surface polypeptide covalently linked to one site on a single stranded oligoribonucleotide, said oligoribonucleotide being linked via a second site to a matrix and being characterized by a nucleic acid sequence complementary to the conserved region of a genome of the pathogenic organism;
   c) incubating the biological fluid and the oligoribonucleotide probe at a temperature and for a time sufficient to allow nucleic acid hybridization to occur without irreversibly destroying the infectivity of the bacteriophage, thereby forming a hybridization mixture;
   d) incubating the hybridization mixture with a ribonuclease at a temperature and for a time sufficient to allow cleavage of all deoxyribonucleic acid-ribonucleic acid hybrids, thereby releasing infective bacteriophage;
   e) measuring the number of infective bacteriophage released in step d, wherein the number of infective bacteriophage released corresponds to the number of pathogen genomes present in the biological fluid.

3. A method for quantitating a pathogenic organism in a biological fluid, the pathogenic organism being characterized by a double stranded deoxyribonucleic acid genome, which method comprises:
   a) processing the biological fluid to release the genome of the pathogen;
   b) combining the biological fluid with an oligoribonucleotide probe comprising a bacteriophage capable of infecting *Lactobacillus lactis*, said bacteriophage having a surface polypeptide covalently linked to one site on a single stranded oligoribonucleotide, said oligoribonucleotide being linked via a second site to a matrix and being characterized by a nucleic acid sequence complementary to a conserved region of the genome of the pathogenic organism;
   c) incubating the biological fluid and the oligoribonucleotide probe at a temperature and for a time sufficient to allow nucleic acid hybridization to occur without irreversibly destroying the infectivity of the bacteriophage, thereby forming a hybridization mixture;
   d) incubating the hybridization mixture with a ribonuclease at a temperature and for a time sufficient to allow cleavage of all deoxyribonucleic acid-ribonucleic acid hybrids, thereby releasing infective bacteriophage;
   e) measuring the number of infective bacteriophage released in step d, wherein the number of infective bacteriophage released corresponds to the number of pathogen genomes present in the biological fluid.

4. A method for quantitating a pathogenic organism in a biological fluid, the pathogenic organism being characterized by a double stranded deoxyribonucleic acid genome, which method comprises:
   a) processing the biological fluid to release the genome of the pathogen;
   b) combining the biological fluid with an oligoribonucleotide probe comprising a bacteriophage capable of infecting attenuated strains of Pseudomonas, said bacteriophage having a surface polypeptide covalently linked to one site on a single stranded oligoribonucleotide, said oligoribonucleotide being linked via a second site to a matrix and being characterized by a nucleic acid sequence complementary to a conserved region of the genome of the pathogenic organism;
   c) incubating the biological fluid and the oligoribonucleotide probe at a temperature and for a time sufficient to allow nucleic acid hybridization to occur without irreversibly destroying the infectivity of the bacteriophage, thereby forming a hybridization mixture;
   d) incubating the hybridization mixture with a ribonuclease at a temperature and for a time sufficient to allow cleavage of all deoxyribonucleic acid-ribonucleic acid hybrids, thereby releasing infective bacteriophage;
   e) measuring the number of infective bacteriophage released in step d, wherein the number of infective bacteriophage released corresponds to the number of pathogen genomes present in the biological fluid.

5. A method for quantitating a pathogenic organism in a biological fluid, the pathogenic organism being characterized by a double stranded deoxyribonucleic acid genome, which method comprises:
   a) processing the biological fluid to release the genome of the pathogen;
   b) combining the biological fluid with an oligoribonucleotide probe comprising a bacteriophage capable of infecting attenuated strains of Salmonella, said bacteriophage having a surface polypeptide covalently linked to one site on a single stranded oligoribonucleotide, said oligoribonucleotide being linked via a second site to a matrix and being characterized by a nucleic acid sequence complementary to a conserved region of the genome of the pathogenic organism;
   c) incubating the biological fluid and the oligoribonucleotide probe at a temperature and for a time sufficient to allow nucleic acid hybridization to occur without irreversibly destroying the infectivity of the bacteriophage, thereby forming a hybridization mixture;

d) incubating the hybridization mixture with a ribonuclease at a temperature and for a time sufficient to allow cleavage of all deoxyribonucleic acid-ribonucleic acid hybrids, thereby releasing infective bacteriophage;

e) measuring the number of infective bacteriophage released in step d, wherein the number of infective bacteriophage released corresponds to the number of pathogen genomes present in the biological fluid.

* * * * *

UNITED STATES PATENT AND TRADEMARK OFFICE
CERTIFICATE OF CORRECTION

PATENT NO. : 5,679,510
DATED : October 21, 1997
INVENTOR(S) : Ray et al.

It is certified that error appears in the above-indentified patent and that said Letters Patent is hereby corrected as shown below:

On the title page, Item [73],

To change the name of the Assignee listed on the face sheet from Hybridon, Inc., Cambridge, Mass. to SymBioTech, Inc., Wellseley, Mass.

Signed and Sealed this

Third Day of August, 1999

*Attest:*

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,679,510
DATED : October 21, 1997
INVENTOR(S) : Ray et al.

It is certified that error appears in the above-indentified patent and that said Letters Patent is hereby corrected as shown below:

change the name of the Assignee listed on the face sheet of the patent from Hybridon, Inc., Cambridge, Mass. to SymBioTech, Inc., Wellseley, Mass.

Signed and Sealed this

Fourteenth Day of December, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: genomic DNA ( v i ) ORIGINAL SOURCE:
        ( A ) ORGANISM: Hepatitis B virus ( i x ) FEATURE:
        ( A ) NAME/KEY: misc_binding
        ( B ) LOCATION: 6..11
        ( D ) OTHER INFORMATION: /bound_moiety= "XbaI Restriction endonuclease"

( x i ) SEQUENCE DESCRIPTION: SEQ ID NO:1:

CAGAGTCTAG ACTCGTGGTG GACTTCTCTC AATTTTCTAG GGGGA    45

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: genomic DNA ( v i ) ORIGINAL SOURCE:
        ( A ) ORGANISM: Hepatitis B virus ( i x ) FEATURE:
        ( A ) NAME/KEY: misc_binding
        ( B ) LOCATION: 12..17
        ( D ) OTHER INFORMATION: /bound_moiety= "AvrII Restriction
            endonuclease"

( x i ) SEQUENCE DESCRIPTION: SEQ ID NO:2:

ACATCAGGAT TCCTAGGACC CCT    23

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: genomic DNA ( v i ) ORIGINAL SOURCE:
        ( A ) ORGANISM: Hepatitis B virus ( i x ) FEATURE:
        ( A ) NAME/KEY: misc_binding
        ( B ) LOCATION: 6..11
        ( D ) OTHER INFORMATION: /bound_moiety= "AatII Restriction
            endonuclease"

( x i ) SEQUENCE DESCRIPTION: SEQ ID NO:3:

CGCGGGACGT CCTTTGT    17

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: genomic DNA ( v i ) ORIGINAL SOURCE:
        ( A ) ORGANISM: Human cytomegalovirus ( i x ) FEATURE:
        ( A ) NAME/KEY: misc_binding
        ( B ) LOCATION: 8..13
        ( D ) OTHER INFORMATION: /bound_moiety= "BglII Restriction
            endonuclease"

( x i ) SEQUENCE DESCRIPTION: SEQ ID NO:4:

CCGGGCAAGA TCTCGCACAT    20

( 2 ) INFORMATION FOR SEQ ID NO:5:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: genomic DNA (vi) ORIGINAL SOURCE:
(A) ORGANISM: Human cytomegalovirus (ix) FEATURE:
(A) NAME/KEY: misc_binding
(B) LOCATION: 8..13
(D) OTHER INFORMATION: /bound_moiety= "BglII Restriction endonuclease"

(xi) SEQUENCE DESCRIPTION: SEQ ID NO:5:

GGGCAGCAGA TCTTCCTGGA 20

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: genomic DNA (ix) FEATURE:
(A) NAME/KEY: misc_binding
(B) LOCATION: 6..11
(D) OTHER INFORMATION: /bound_moiety= "XbaI Restriction endonuclease"

(xi) SEQUENCE DESCRIPTION: SEQ ID NO:6:

CAGAGTCTAG ACTCGTGGTG 20

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: mRNA (vi) ORIGINAL SOURCE:
(A) ORGANISM: Hepatitis C virus (xi) SEQUENCE DESCRIPTION: SEQ ID NO:7:

GCGAAAGGCC UUGUGGUACU G 21

(2) INFORMATION FOR SEQ ID NO:8:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: mRNA (ix) FEATURE:
(A) NAME/KEY: misc_binding
(B) LOCATION: 9..14
(D) OTHER INFORMATION: /bound_moiety= "SmaI Restriction endonuclease"

(xi) SEQUENCE DESCRIPTION: SEQ ID NO:8:

CCCCCCCUCC CGGGAGAGCC A 21